(12) United States Patent
van Veen

(10) Patent No.: US 11,478,381 B2
(45) Date of Patent: Oct. 25, 2022

(54) DEVICE, SYSTEM AND METHODS FOR COMPENSATING FOR PARTIAL LOSS OF VISUAL FIELD

(71) Applicant: Holding HemiGlass B.V., Hoensbroek (NL)

(72) Inventor: Nico Eduard van Veen, Hoensbroek (NL)

(73) Assignee: Holding HemiGlass B.V., Hoensbroek (NL)

( * ) Notice: Subject to any disclaimer, the term of this patent is extended or adjusted under 35 U.S.C. 154(b) by 59 days.

(21) Appl. No.: 16/978,781

(22) PCT Filed: Mar. 8, 2019

(86) PCT No.: PCT/EP2019/055873
§ 371 (c)(1),
(2) Date: Sep. 8, 2020

(87) PCT Pub. No.: WO2019/170872
PCT Pub. Date: Sep. 12, 2019

(65) Prior Publication Data
US 2020/0405543 A1    Dec. 31, 2020

Related U.S. Application Data

(60) Provisional application No. 62/641,027, filed on Mar. 9, 2018.

(30) Foreign Application Priority Data

Mar. 9, 2018  (NL) ...................................... 2020562

(51) Int. Cl.
G02B 27/00   (2006.01)
A61F 9/08    (2006.01)
(Continued)

(52) U.S. Cl.
CPC ................ *A61F 9/08* (2013.01); *B33Y 80/00* (2014.12); *G02B 27/017* (2013.01);
(Continued)

(58) Field of Classification Search
CPC ......... A61F 9/08; B33Y 80/00; G02B 27/017; G02B 27/0916; G02B 27/1066;
(Continued)

(56) References Cited

U.S. PATENT DOCUMENTS 4,698,857 A * 10/1987 Kastendieck .......... G02B 5/003
2/426
6,088,165 A * 7/2000 Janeczko ............. G02B 23/125
250/214 VT (Continued)

FOREIGN PATENT DOCUMENTS

ES      2542804       8/2015
WO    2016149536      9/2016

*Primary Examiner* — Frank F Huang
(74) *Attorney, Agent, or Firm* — N.V. Nederlandsch Octrooibureau

(57) ABSTRACT

A device (100) for compensating for part of the visual field comprises a wearable frame (110) configured to rest upon the face of a subject. An image capture device (120) is configured to capture an image from a first region (20) of the subject's visual field the first region being identified as a region of the visual field in which the subject's vision is impaired, and relay the image to an image display unit (130). The image display unit (130) is configured to project the image onto a region of the subject's retina that corresponds to a second region of the subject's visual field, in which the subject's vision is identified as non-impaired. Associated methods are also described.

16 Claims, 8 Drawing Sheets

(51) Int. Cl.
*B33Y 80/00* (2015.01)
*G02B 27/01* (2006.01)
*G02B 27/09* (2006.01)
*G02B 27/10* (2006.01)
*G02B 27/64* (2006.01)

(52) U.S. Cl.
CPC ..... *G02B 27/0916* (2013.01); *G02B 27/1066* (2013.01); *G02B 27/642* (2013.01); *G02B 2027/0138* (2013.01); *G02B 2027/0178* (2013.01)

(58) Field of Classification Search
CPC .......... G02B 27/642; G02B 2027/0138; G02B 2027/0178
USPC .......................................................... 348/62
See application file for complete search history.

(56) References Cited

U.S. PATENT DOCUMENTS

| | | | | |
|---|---|---|---|---|
| 6,560,029 B1* | 5/2003 | Dobbie | ................ | G02B 23/125 |
| | | | | 2/6.1 |
| 9,279,983 B1* | 3/2016 | Davis | .................... | G06F 3/0488 |
| 9,615,067 B1* | 4/2017 | Foote | ..................... | H04N 7/185 |
| 9,811,154 B2* | 11/2017 | Raffle | ..................... | G06F 3/011 |
| 9,917,957 B1* | 3/2018 | Martin | .................... | H04N 1/387 |
| 10,101,891 B1* | 10/2018 | Kulewski | ............. | G06F 3/04845 |
| 10,244,175 B2* | 3/2019 | Khoe | ..................... | G06T 3/0012 |
| 10,341,564 B1* | 7/2019 | Derbanne | .......... | H04N 5/23258 |
| 10,432,864 B1* | 10/2019 | Douady | ............... | H04N 5/2253 |
| 10,586,528 B2* | 3/2020 | Manuvinakurike | ... | G10L 15/063 |
| 10,607,313 B2* | 3/2020 | Jenny | ........................ | G06T 3/005 |
| 10,796,445 B2* | 10/2020 | Yerkes | ................... | G06T 19/006 |
| 10,861,159 B2* | 12/2020 | Romanenko | ............. | G06T 7/73 |
| 10,962,780 B2* | 3/2021 | Ambrus | .................. | G06F 3/011 |
| 2003/0231804 A1* | 12/2003 | Bacarella | ............. | H04N 5/2624 |
| | | | | 382/284 |
| 2006/0291849 A1* | 12/2006 | Shamir | ................... | G03B 17/00 |
| | | | | 396/334 |
| 2008/0170119 A1* | 7/2008 | McCann | ................ | H04N 7/181 |
| | | | | 348/113 |
| 2009/0251680 A1* | 10/2009 | Farsaie | ................... | G01S 17/89 |
| | | | | 356/3 |
| 2010/0128135 A1* | 5/2010 | Filipovich | .......... | G02B 27/0172 |
| | | | | 348/217.1 |
| 2015/0133901 A1* | 5/2015 | Serdarevic | ............ | A61F 9/0079 |
| | | | | 606/5 |
| 2016/0310325 A1* | 10/2016 | Jiao | .......................... | G02C 7/00 |
| 2017/0078623 A1* | 3/2017 | Hilkes | ................ | G02B 27/0172 |
| 2017/0092007 A1* | 3/2017 | Goldberg | ............ | G06K 9/00597 |
| 2018/0125716 A1* | 5/2018 | Cho | .......................... | G06F 3/011 |
| 2020/0405543 A1* | 12/2020 | van Veen | ............. | G02B 27/017 |

* cited by examiner

*Fig. 9*

```
providing patient information identifying (i) a first region of the subject's visual
field in which the vision is identified as impaired and (ii) a second region of the
subject's visual field in which vision is identified as non-impaired
```

```
providing a wearable frame comprising a first arm, a second arm and a bridging
portion configured to extend between the first arm and the second arm and rest
on the face of the subject
```

```
based on the identification of the first region, mounting an image capture device
on the wearable frame to capture an image from the first region of the subject's
visual field
```

```
based on upon identification of the second region, mounting an image display
unit on the frame to project the captured image onto a region of the patient's
retina that corresponds to the second region of the subject's visual field
```

*Fig. 10*

(a) providing patient information identifying (i) a first area of the subject's visual field in which the subject's visual field is identified as impaired and (ii) a second region of the visual field in which the subject's visual field is identified as non-impaired (b) capturing an image from the first area of the subject's visual field using an image capture device (120)

(c) cropping the captured image based on image cropping information, wherein the image cropping information is based on the first region (20) as identified in step (a)

(d) projecting the cropped image onto a region of the subject's retina that corresponds to the second region of the subject's visual field as identified in step (a)

DEVICE, SYSTEM AND METHODS FOR COMPENSATING FOR PARTIAL LOSS OF VISUAL FIELD

FIELD OF THE INVENTION

The present invention relates to devices, systems and methods for addressing or compensating for partial loss of vision in a subject. More particularly, the present invention relates to a device, system and method for compensating for loss of part of the visual field (e.g. hemianopsia) by displaying in the surviving visual field a live video feed showing all or part of the lost visual field.

BACKGROUND OF THE INVENTION

Normal binocular visual field in humans extends up to approximately 90 to 100 degrees temporally (away from the nose in each direction) and approximately 50 to 60 degrees superiorly (upwards) and 70 to 75 degrees inferiorly. Visual field loss (loss of vision in a part of the visual field) may occur due to disease or trauma to the eye or brain (including the optic pathways). Several conditionals may cause loss of part of the visual field. For example, vision loss may occur when the optic pathways to the brain are damaged during as a result of a brain injury. The most common causes are stroke, brain tumour or trauma, although other causes have been reported. However, loss of part of the visual field may also arise due to near or total blindness in one eye or the loss of an eye.

Hemianopsia is impaired vision or blindness in part of the visual field. Most commonly, hemianopsia manifests itself as blindness in half of the visual field although blindness in more or less than half of the visual field is also possible. The most common types of hemianopsia include homonymous hemianopsia (blindness on the same side of the vertical mid line in both eyes, resulting in loss of one side of the visual field), heteronymous hemianopsia (loss of vision on different sides of both eyes, resulting in loss of the central or peripheral visual field), superior hemianopsia (loss of the upper half of the visual field in both eyes) and inferior hemianopsia (loss of the lower half of the visual field in both eyes), and quadrantic hemianopsia (loss of one quarter of the visual field in one or both eyes). Other proportions of the visual field may also be lost or lost to a different degree, depending on the location and severity of the brain injury and the resulting disruption to the optic pathways.

Current treatments for partial visual field loss include saccadic eye movement training, optical visual field expanders and vision restoration therapy.

Saccadic eye movement therapy involves teaching the patient to move their eyes to expand their field of vision by scanning the area of field that is missing. One of the drawbacks of saccadic eye movement therapy as a treatment for hemianopsia is that many patients with brain injuries resulting in loss of visual field may also struggle to perform the necessary eye movements for scanning.

Optical field expanders rely on prescription eyewear that expands the visual field of the patient using optical elements. Examples include peripheral prism visual field expanders, as described in "*Community-based trial of a peripheral prism visual field expansion device for hemianopia*", Bowers et al, Arch Ophthalmol. 2008 May; 126(5): 657-64.

Vision restoration therapy (VRT) describes treatments that seek to restore the lost visual field by stimulation around the periphery of the region in which the visual field has been lost. Typically, such VRT requires the patient to focus of a focal point and respond whenever they perceive a light appear around the focal point. The lights are programmed to appear around the edge of the lost visual field. With time, the user trains the impaired but surviving visual function around the edge of the lost visual field, thus improving their overall visual field.

SUMMARY OF THE INVENTION

The present invention seeks to provide devices and methods that can at least partially compensate for the loss of part of the visual field in a subject.

In a first aspect of the invention there is provided a device for compensating for partial loss of visual field in a subject, the device comprising: a wearable frame comprising a first arm, a second arm and a bridging portion configured to extend between the first arm and the second arm and rest on the face of the subject; an image capture device supported by the wearable frame and configured to capture an image from a first region of the subject's visual field; a display unit configured to project the captured image onto a region of a retina of the subject corresponding to a second region of the subject's visual field; wherein the first region of the subject's visual field is identified as a region of the subject's visual field in which the subject's vision is impaired and the second region of the visual field is identified as a region of the subject's visual field in which the subject's vision is deemed non-impaired. Optionally, the display unit can be configured to crop the image based on stored cropping information before projecting the image onto the region of the retina of the subject, wherein the stored cropping information is based on patient information identifying the first region and the second region of the visual field.

In a second aspect of the invention there is provided a method for manufacturing a device for compensating for partial loss of visual field in a subject, the method comprising: providing patient information identifying (i) a first region of the subject's visual field in which the vision is identified as impaired and (ii) a second region of the subject's visual field in which vision is identified as non-impaired; providing a wearable frame comprising a first arm, a second arm and a bridging portion configured to extend between the first arm and the second arm and rest on the face of the subject; based on the identification of the first region, mounting an image capture device on the wearable frame to capture an image from the first region of the subject's visual field; based on upon identification of the second region, mounting an image display unit on the frame to project the captured image onto a region of the subject's retina that corresponds to the second region of the subject's visual field. Optionally, the display unit can be configured to crop the image based on stored cropping information before projecting the image onto the region of the retina of the subject, wherein the stored cropping information is based on patient information identifying the first region and the second region of the visual field.

In a third aspect of the invention, there is provided a method for compensating for partial loss of visual field in a subject, the method comprising: (a) providing patient information identifying (i) a first area of the subject's visual field in which the subject's visual field is identified as impaired and (ii) a second region of the visual field in which the subject's visual field is identified as non-impaired; (b) capturing an image from the first area of the subject's visual field using an image capture device; (c) projecting the captured image onto a region of the subject's retina that corresponds to the second region of the subject's visual field as identified in step (a). Optionally, the display unit can be configured to crop the image based on stored cropping information before projecting the image onto the region of the retina of the subject, wherein the stored cropping information is based on patient information identifying the first region and the second region of the visual field.

In a fourth aspect of the invention, there is provided an image display unit provided with at least one light source for delivery of photons to an eye for use in a method for the treatment of hemianopsia characterized in that the light source of the image display emits photons building up an image onto a region of a subject's retina that corresponds to a second region of the subject's visual field in which the subject's vision is identified as non-impaired, therewith compensating for partial loss of visual field in the subject, the method comprising: (i) identifying a first region of the subject's visual field in which the subject's visual field is impaired; (ii) capturing the image from the first region of the subject's visual field using an image capture device; (iii) displaying the image captured by the image capture device on the image display, wherein the displayed image is optionally cropped based on image cropping information relating to the first area identified in step (i); (iv) projecting the displayed image onto the region of the subject's retina that corresponds to the second region of the subject's visual field in which the subject's vision is identified as non-impaired. In at least some embodiments, the image display can be provided with at least one light source for delivery of photons to an eye, wherein the image display comprises at least one light emitting diode comprising the light source and wherein the light source is a semiconductor material such as a p/n semiconductor material.

In any of the above inventive aspects, the display unit can be configured to crop the captured image to correspond to the first region. In some embodiments, the cropped image can extend beyond the first region to provide at least one region of overlap with the second region. In such embodiments, the cropped image can comprise a first portion captured from the first region and a second portion captured from the second region, wherein the second region occupies between 5% and 20% of the area of the cropped image (e.g. 10% of the area of the cropped image).

The display unit can comprise a display configured to display the captured image and an optical element configured to project the image onto the region of the subject's retina. The display can comprise a screen and/or a projector. In at least some embodiments, the optical element can comprises a lens, a prism, a mirror or any combination thereof, configured to allow the user to focus on the image displayed by the display unit.

Preferably, the device further comprises a rechargeable power source. The rechargeable power source may comprise a battery rechargeable by inductive charging.

The image capture device can mounted on a central portion of the bridging portion of the wearable frame (e.g. in a region between the user's eyes) or the image capture device can be mounted to one side of the frame (e.g. on one of the support arms). In at least some embodiments, the wearable frame can comprise a frame for a pair of spectacles comprising a first lens supporting portion coupled to the first arm, a second lens supporting portion coupled to the second arm and a nose bridge portion connecting the first and second lens supporting portions. Alternatively, the frame can comprise a different structure configured to be worn by the user and display an image to the user in a perceivable manner. For example, the frame can comprise a single arm and an additional support portion configured to rest on the nose of the wearer. Other wearable frame configurations will be apparent to the skilled person.

In any of the above described aspects of the invention, the patient information can comprises a hemianopsia classification. A hemianopsia classification can include homonymous hemianopsia, heteronymous hemianopsia, superior hemianopsia and inferior hemianopsia, and quadrantic hemianopsia or other visual field loss classifications.

The patient information can also comprise an individualised visual field map identifying at least one of: (i) the first area of the subject's visual field in which vision is identified as impaired; and (ii) the second area of the subject's visual field in which vision is identified as non-impaired. The field map can be produced by monocular perimetry testing or binocular perimetry testing.

Methods according to aspects of the present invention can further comprise the step of mapping the subject's visual field and identifying (i) the first area of visual field in which vision is identified as impaired; and (ii) the second area of visual field in which vision is identified as non-impaired.

Method according to aspects of the present invention can further comprise the step of configuring the display unit to crop the captured image based on the patient information. The cropped image can corresponds to the first region (e.g. the captured image shows an image extending across the first (missing) region of the visual field but no further). The cropped image can extend beyond the first region to provide at least one region of overlap with the second region. The region of overlap can be between 5% and 20% of the area of the displayed image, e.g. 10%. The overlap between the captured image and the unimpaired visual field allows the user to correctly place the captured image relative to their surroundings.

In at least some embodiments of the above described aspects, the patient information can be stored in a storage medium comprises in the device. The device can comprise connection means (e.g. a wired or wireless connection) that allows patient information to be uploaded to the device. The device can further comprise processing means configured to appropriately crop the image and/or orient the camera based on the stored patient information.

For any of the above described aspects, the display unit can be configured to show a live video feed from the image capture device. In at least some embodiments, the frame can be formed using an additive manufacturing technique.

BRIEF DESCRIPTION OF THE DRAWINGS

The present invention will now be described by way of example with reference to the accompanying drawings, in which:

FIG. 9 shows schematically the steps of a method for manufacturing a device according to the present invention;

FIG. 10 shows schematically the steps of a method for compensating for loss of visual field in a subject.

DETAILED DESCRIPTION OF ILLUSTRATIVE EMBODIMENTS

Figure 1:
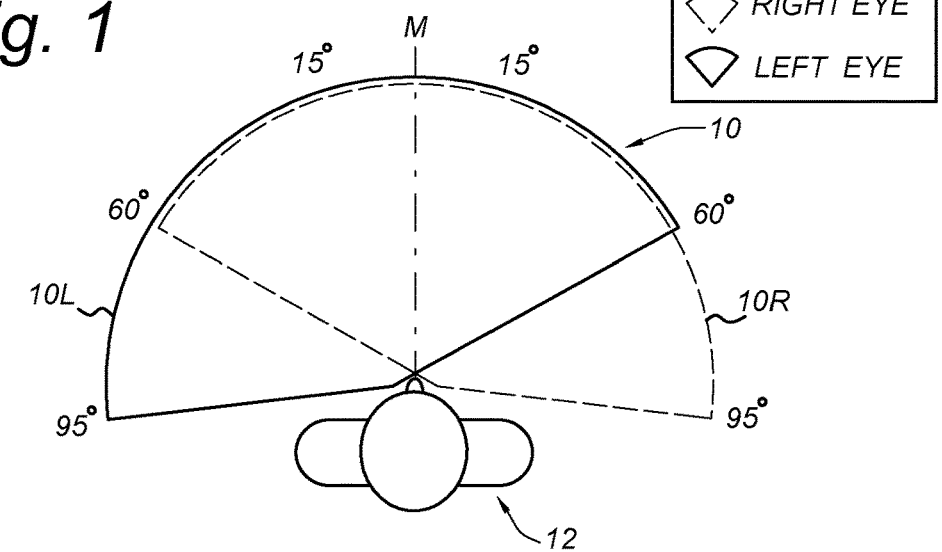
FIG. 1 shows a schematic of the approximate unimpaired visual field of a human.

FIG. 1 shows the approximate unimpaired visual field 10 of a human 12. As shown in FIG. 1, the unimpaired visual field 10 extends temporally approximately 95 degrees from the vertical midline M in either direction. In the schematic shown in FIG. 1, the visual field of the right eye 10R extends to approximately 95 degrees from the midline M towards the right ear and approximately 60 degrees from the midline towards the left ear. Similarly, the visual field of the left eye 10L extends to approximately 95 degrees from the midline M towards the left ear and approximately 60 degrees from the midline M towards the right ear. In the region extending temporally to approximately 60 degrees from the midline M in either direction, the visual field for the right eye overlaps with the field of view of the left eye and vision is binocular. From approximately 60 degrees from the midline M to approximately 95 degrees from the midline M (in either direction) the visual field is monocular.

Loss of part of the visual field can result from a brain injury or another disease or disorder that affects the optic pathways within the brain. For example, up to 30% of people that have suffered a stroke will experience some loss of vision, which often manifests as loss of part of the visual field. Most commonly, loss of visual field is in one half of both eyes (known as homonymous hemianopsia), which results in half of the subject's visual field being missing or impaired. Other regions of the visual field can also be lost, to a greater and lesser extent. Visual field and the degree to which a subject's visual field is lost or impaired is measured by perimetry. In kinetic perimetry tests, visual markers (e.g. spots of light) are shown on the interior of a partial sphere extending away from a focal point upon which the subject focuses. The spots or markers are moved slowly towards the subject's focal point until the subject indicates that they can perceive the spots. In static perimetry tests, light spots are flashed at varying intensities at fixed locations on the interior surface of the partial sphere and the user is invited to indicate when they observe a light spot. The location of the spots that the subject can see and the location of the spots that the user cannot see provide a map of the impaired and unimpaired visual field. Visual field tests can be carried out for binocular vision (indicating the overall impact of the loss of vision on the visual field) and for each eye individually (indicating the degree to which the vision in each eye is impaired).

Figure 2:
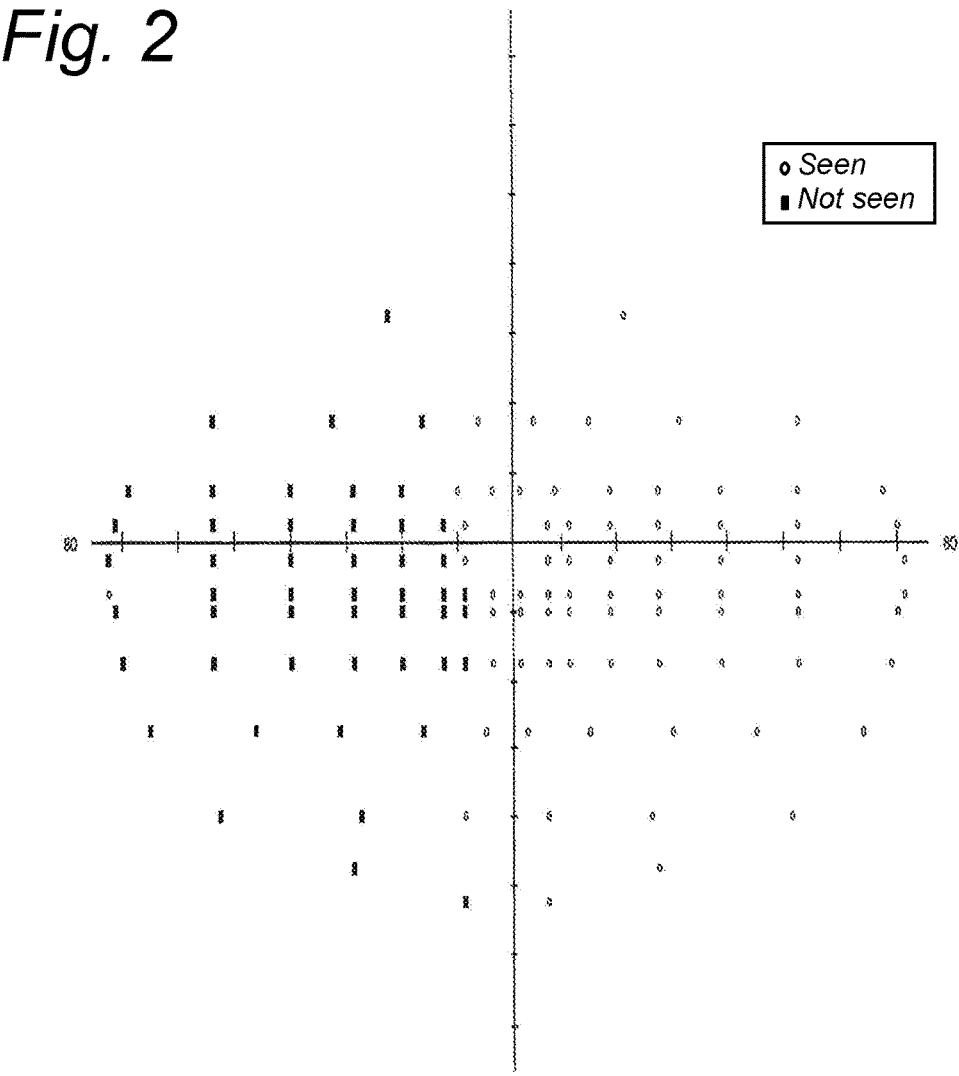
FIG. 2 shows the results of a binocular visual field test for a test subject A suffering from visual field impairment following a brain injury.

FIG. 2 shows the results of a binocular visual field test (Esterman automated static perimetry testing) for a test subject A suffering from homonymous hemianopsia. During the test, individual spots of light were shown on the interior of a hemisphere, with the subject focusing on a predetermined point (the central point on the interior of a hemispherical surface). The subject was invited to indicate when they perceived that a spot of light appeared on the interior of the sphere. The location of the light and the response (or absence thereof) from the subject was recorded. FIG. 2 shows the location of lights appearing on the interior of the screen and, as indicated by the legend, whether the subject was able to perceive the spots of light or not. As seen from FIG. 2, test subject A was able to perceive all of the light spots that appeared on the right hand side of the screen (e.g. to the right of a vertical centre line passing through the focal point). However, of 60 light spots shown to the left of the vertical centreline of the screen, the test subject only identified ten, all of which were clustered close to the centreline of the screen. The test thus demonstrated that the left side of subject A's visual field is significantly compromised, with almost half of the visual field being completely absent.

Figure 3A:
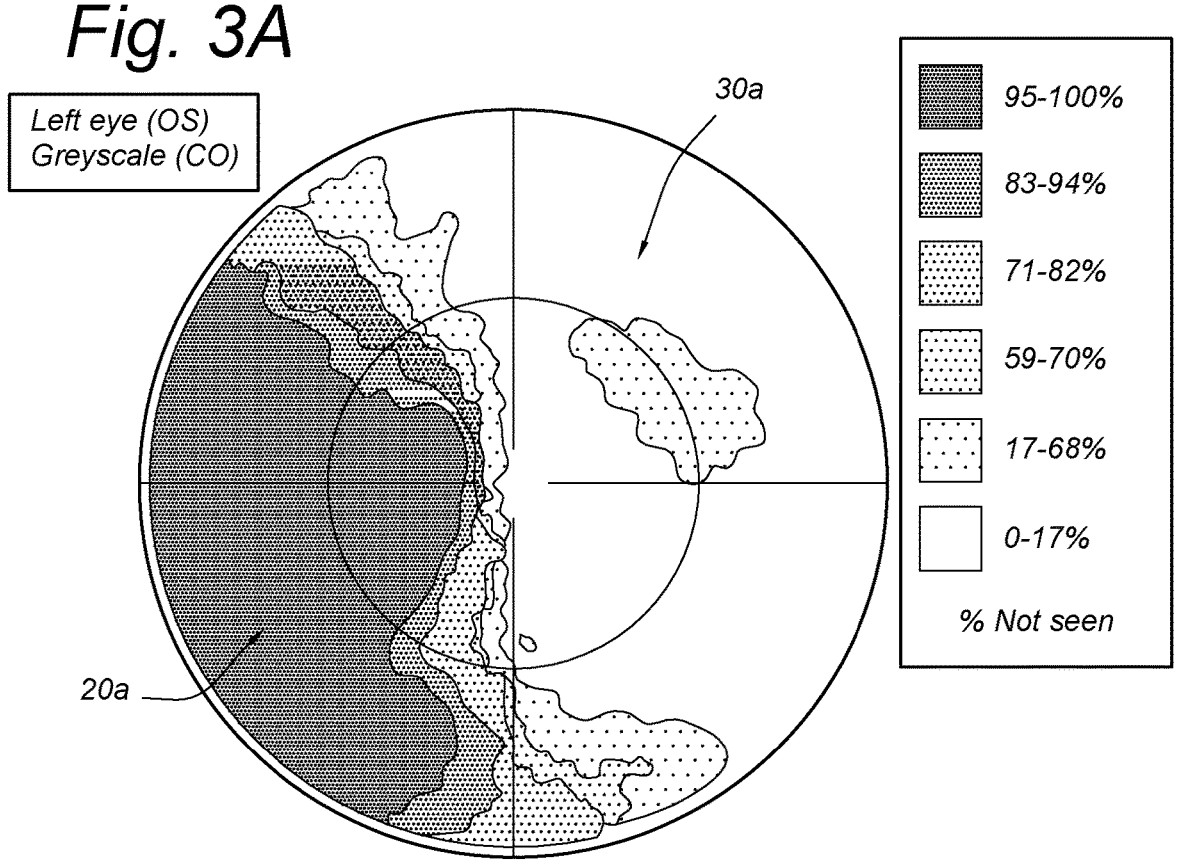
FIG. 3A shows a monocular visual field test for the left eye of the test subject A for whom test results are shown in FIG. 2.
Figure 3B:
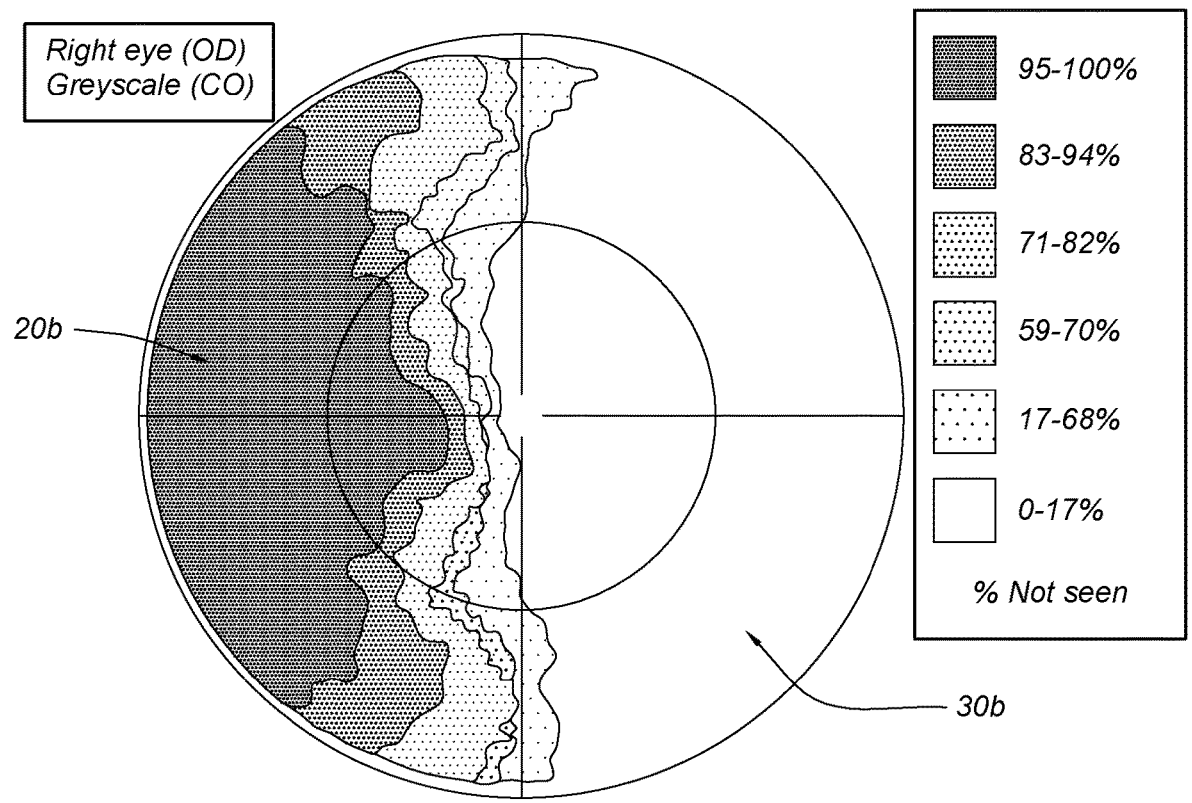
FIG. 3B shows a monocular visual field test for the right eye of the test subject A for whom test results are shown in FIG. 2.

FIGS. 3A and 3B show the results of monocular static perimetry tests carried out with test subject A for each eye. FIG. 3A shows the results for test subject A's left eye and FIG. 3B shows the results for test subject A's right eye. For each eye, the compromised (20a, 20b) and uncompromised (30a, 30b) regions of the visual field were mapped. Because the right half of the brain has visual pathways for the left hemifield of both eyes, and the left half of the brain has visual pathways for the right hemifield of both eyes, damage in the right half of the brain leads to visual defects that correspond to loss of vision from the left half of each retina (and loss of vision in the right part of the visual field). Note that in the context of the present application a region of the retina is considered compromised if the user cannot perceive images incident on this portion of the retina. This may be due to direct damage to the retina (e.g. due to trauma, although this would rarely affect both eyes equally to result homonymous hemianopsia) or it may be due to a brain injury or disorder that results in the optic pathways being disturbed. This is the most common mechanism by which stroke results in partial loss of visual field.

From FIG. 2, it can be seen that test subject A has loss of vision in the left half of the visual field, corresponding to loss of vision from the right half of each retina (caused by a stroke in the right half of the brain). This is confirmed by the results of the monocular perimetry test shown in FIG. 3A, which shows a first region 20a in which visual field from the left eye is compromised and a second region 30a in which visual field for the left eye in which vision is not compromised. Similarly, for the right eye test shown in FIG. 3B, a first region 20b exists in which visual field from the right eye is compromised and a second region 30b in which visual field for the right eye in which vision is not compromised. This results in the loss of binocular visual field demonstrated by the perimetry test results shown in FIG. 2.

Figure 4:
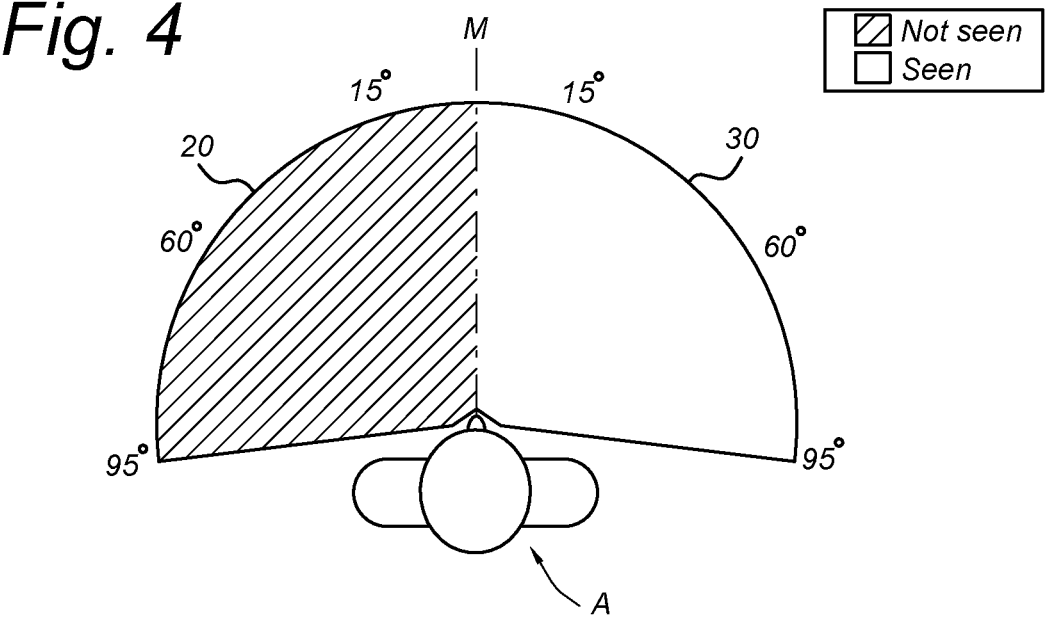
FIG. 4 shows a schematic of the approximate visual field for the test subject A from FIG. 2.

The impact that subject A's loss of vision has on her binocular visual field is shown schematically in FIG. 4. As shown in FIG. 4, subject A's visual field can be divided into two regions: (i) a first region 20 in which vision is impaired or missing entirely; and (ii) a second region 30 in which vision is not deemed impaired. It will be appreciated that the criteria for identifying impaired and non-impaired vision can be determined by a healthcare professional. For example, a threshold can be chosen (e.g. a light intensity threshold in an Esterman static perimetry test) above which a user's failure to perceive a marker is deemed a determined as a "fail" result. The region in which "fail" results are returned can be deemed impaired. Where the user is able to perceive the marker, the marker is identified as a "pass". The region in which "pass" results are returned can be deemed "unimpaired", even if the subject's vision is not perfect in this region (e.g. if prescription lenses are deemed appropriate).

This can be assessed on an individual basis by a healthcare professional or other visual field assessor.

Embodiments of the present invention seek to compensate for the loss of part of the visual field in a subject (such as test subject A) by capturing an image from the first region 20 of the visual field, which is identified as impaired, and delivering the image to an uncompromised region of the retina in which the user can perceive the image. In practice, this can be done by positioning an image capture device (such as a camera) in a position in which it captures an image from the first region 20 of the visual field in which vision is identified as impaired. A display unit can then project the captured image to a region of the subject's retina in which vision is not compromised. The region of the retina that is not compromised is the region of the retina that corresponds to the second region 30 of the subject's visual field.

Figure 5A:
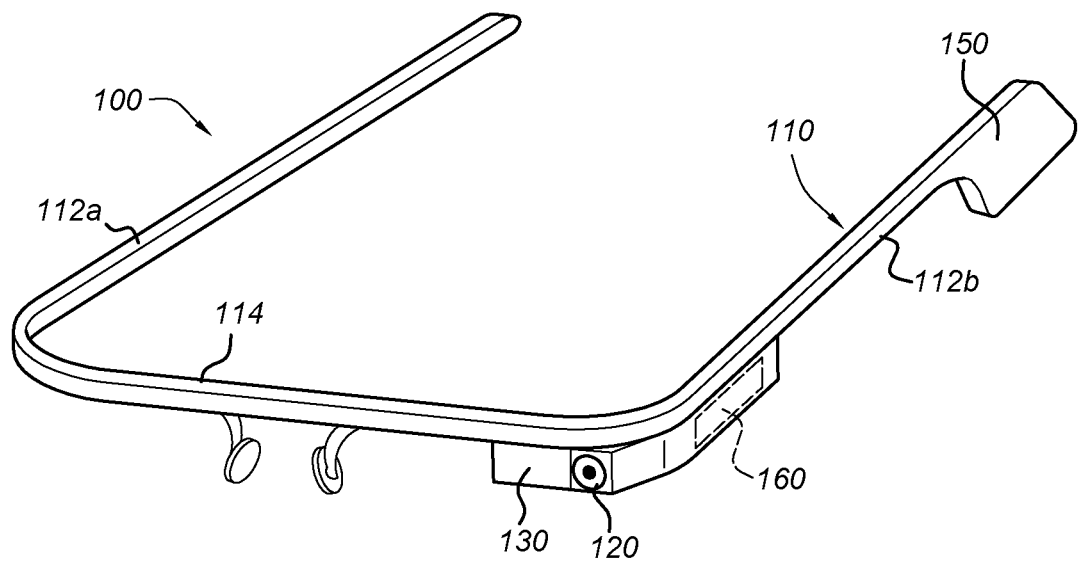
FIGS. 5A and 5B each show a schematic of a device for compensating for visual field loss according to embodiments of the present invention.
Figure 5B:
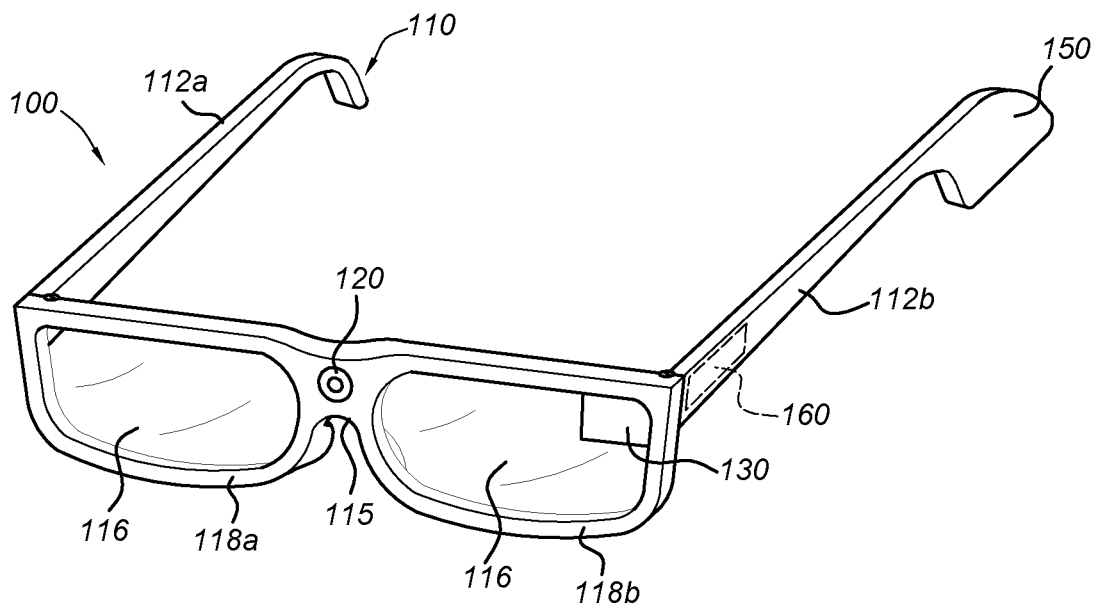

Referring now to FIGS. 5A and 5B, devices 100 according to the present invention comprise a wearable frame 110 comprising a first arm 112a, a second arm 112b and a bridging portion 114 configured to extend between the first arm 112a and the second arm 112b and rest on the face of the subject. An image capture device 120 (e.g. a video camera) is supported by the wearable frame and is configured to capture an image from the first (impaired) region 20 of the subject's visual field. A display unit 130 is configured to project the captured image onto a region of a retina of the subject corresponding to the second (unimpaired) region 30 of the subject's visual field. Preferably, the image capture device 120 relays a live video stream to the display unit 130.

As shown in FIGS. 5A and 5B, the wearable frame 110 can take different forms. For example, as shown in FIG. 5A, the frame 110 can include a frame configured to rest on the bridge of a subject's nose. The frame supports the display unit 130 and the image capture device 120, but does not include the lenses or lens supporting portions of a convention pair of spectacles. Alternatively, as shown in FIG. 5B, the wearable frame 110 can take the form of a conventional pair of spectacles, comprising a pair of lenses 116 and first and second lens supporting portions 118a, 118b. In some embodiments, one or both of the lenses can be a prescription lens or a plain lens. The lenses 116 may also be omitted entirely.

The image capture device 120 is positioned such that it captures an image from the first region 20 of the subject's visual field. The placement of the image capture device 120 can be determined depending on the subject's visual field loss. For example, for test subject A described above with reference to FIGS. 2 to 4, the image capture device 120 can be positioned to capture an image from the left part of the subject's visual field. It will be appreciated that the visual field is determined by reference to the subject. Therefore, the position of the image capture device 120 relative to the frame 110 is determined by reference to the position of the frame with respect to the subject, when worn, and the subject's visual field with forward gaze. In other words, the position of the image capture device 120 is determined such that the field of view of the image capture device 120 encompasses at least part of the subject's impaired or missing visual field 20 when the device 100 is worn by the subject. As shown in FIG. 5A, the image capture device 120 can be mounted to one side of the wearable frame 110, e.g. on one of the support arms 112a, 112b. Alternatively, as shown in FIG. 5B, the image capture device 120 can be mounted on the bridging portion 114 of the wearable frame 110. In either case, the image capture device can be oriented such that it points towards the missing visual field, e.g. in a direction along the midline of the missing visual field 20. In other embodiments, the image capture device 120 can be oriented in a forward direction with respect to the subject (e.g. along the midline M of the standard visual field 10 as shown in FIG. 1). In such embodiments, the image capture device can comprise a wide angle lens.

The image display unit 130 is mounted on or supported by the frame 110. The display unit 130 is configured to project the captured image onto an uncompromised region of the subject's retina. An uncompromised region may be determined using perimetry testing (e.g. monocular perimetry testing) as described above. The display unit 130 can comprise a display 132 configured to display the image captured by the image capture device 120 and an optical element 134 configured to project the displayed image onto the subject's retina. The image displayed by the display unit 130 can be a live video feed from the image capture device 120.

It will be appreciated that when the display is mounted on the wearable device, the image is displayed in the very near field of the subject's vision. To ensure that the user can focus on the image displayed by the display 132, the optical element 134 can be provided to map the up-close view to a wide field of view (i.e. to allow the eye to focus on a virtual image of the display that appears further away and that the subject is able to focus on). In practice, this may mean providing a converging or collimating optical element (with positive optical power) to create a virtual image of the display at a distance further from the subject's eye than the real image. The display 132 and the optical element 134 can take different forms, and methods of allowing the user to focus on the projected image will be apparent to the skilled person. Suitable optical arrangements for allowing the user to focus on an up-close display may include prisms, lenses, mirrors, SLM projectors, etc. e.g. optical elements or combinations of optical elements with positive optical power. It should be noted that the term "project" herein is not intended to limit the present invention to displays comprising a projector. Instead, the term project is used to mean that the image is delivered or projected onto the subject's retina so that the user is able to perceive and focus on the image. In practice, this may mean creating a virtual image at a distance of at least 150 mm away from the subject's pupil, although the skilled person will appreciate that this will depend on the subject's near sight.

Figure 6A:
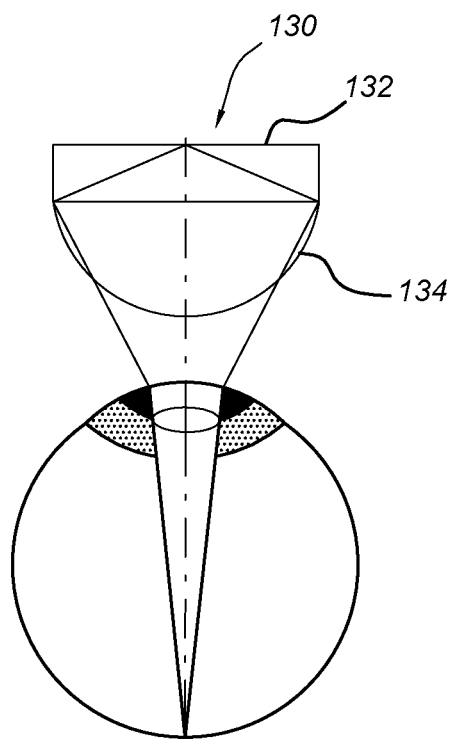
FIGS. 6A and 6B show display units suitable for use with embodiments of the present invention.

In at least one embodiment of the present invention, the display unit 130 can comprise a display 132 and an optical element 134 provided as separate elements. For example, referring now to FIG. 6A, the display 132 can comprise a screen (e.g. an LED or LCD screen) and the optical element 134 can comprise a lens configured to allow the subject to focus on the image displayed on the screen 132. In other embodiments, the display 132 and the optical element 134 (that allows the user to focus on the displayed image) can be integrated.

Figure 6B:
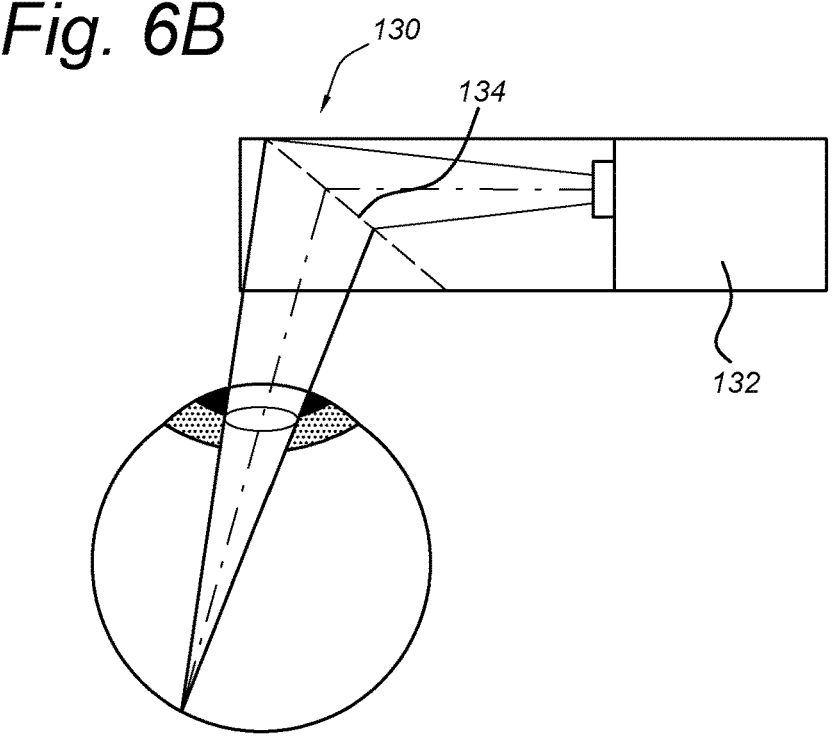

Turning now to FIG. 6B, as an alternative to the screen display described above, the display 132 can comprise a projector and the optical element 134 can comprise a prism configured to project the image from the projector directly onto the retina. Projector arrangements suitable for use in connection with the present invention are described in US2014/0320755 A1, which is herein incorporated by reference. The optical element 134 can be configured to allow the user to vary the focus, thereby allowing optimisation of the focus for the individual user. In both cases, the skilled person will also appreciate that the optical element 134 can be a single optical element with optical power (e.g. a single or prism lens with optical power) or it can be a composite optical element comprising multiple components.

As explained above, the display unit 130 is configured to project the image from the image display 132 onto a region of the user's retina that is identified as corresponding to an area of the visual field that is not deemed impaired, i.e. a region of the retina from which vision is not compromised. The precise configuration of the display unit 130 can thus be chosen depending on the location and the degree of the user's loss of visual field. By capturing an image from the area of the visual field that is missing or impaired for a particular subject and projecting the captured image onto an uncompromised portion of the retina, the user is able to perceive the previously missing visual field.

The location of the display and/or the configuration of the optical elements and the image capture device can be chosen based on the subject's needs. For example, for optimal results, the image capture device 120 and the display unit 130 can be mounted on the frame such that they obscure as little as possible of the subject's unimpaired visual field 30.

In some embodiments of the present invention, the display unit 130 can be configured to crop the image captured by the image capture device 120 based on cropping information. The cropping information ca be based on patient information representing the extent of visual field loss of the subject, e.g. information identifying (i) the first region 20 of the subject's visual field in which vision is impaired and (ii) the second region 30 of the visual field in which is the subject's visual field is deemed non-impaired. Cropping the image (either by limiting the field of view of the image capture device 120 or by cropping the received image before displaying the image on display 132) minimises duplication of and redundancy in the subject's field of view by displaying a field of view to the subject that is most relevant for compensating for the subject's visual field loss. For example, the image can be cropped to correspond to the first region 20 (shown in FIG. 4) in which a subject's vision is identified as impaired. This minimises redundancy in the displayed image by ensuring that the parts of the visual field that the user is able to perceive (second region 30) are not prioritised on the display device 132. In some embodiments, it may be preferable to crop the image to provide a region of overlap between the captured image and the second (unimpaired) region 30. Overlap between the cropped image and the second region 30 can allow the subject to correctly place the captured image (from the first region 30) relative to the second region (region 30).

Figure 7:
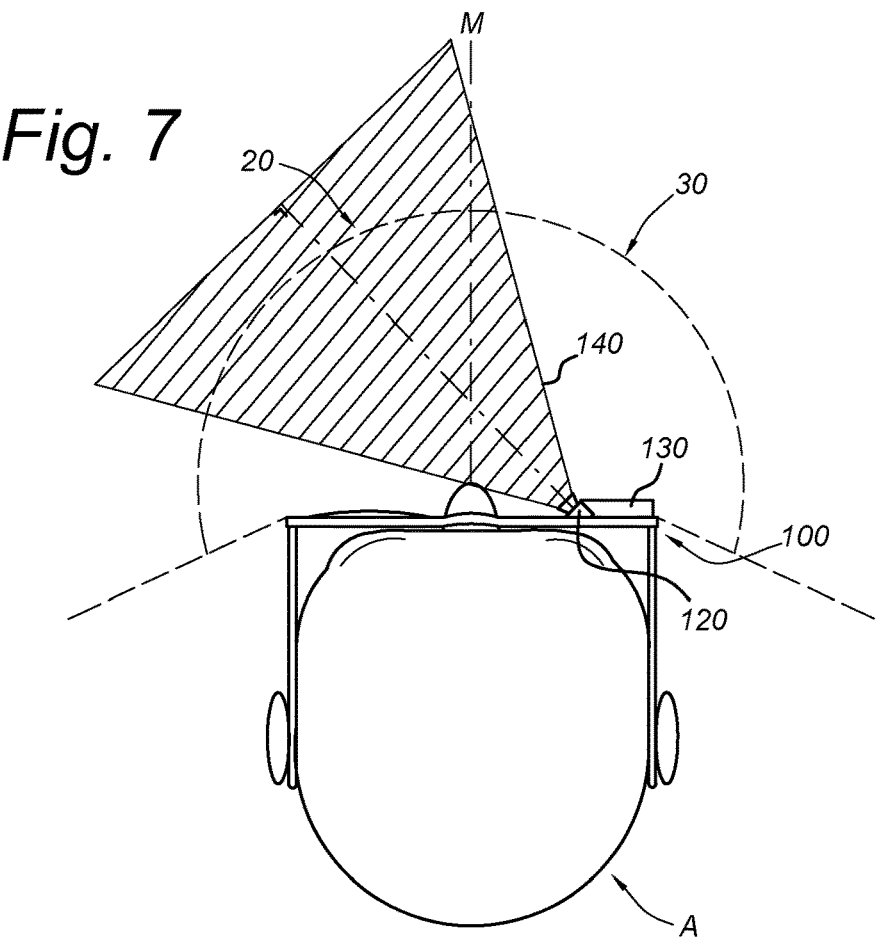
FIG. 7 shows a top view of a subject wearing a device according to an embodiment of the present invention.

For example, the cropped image can comprise a first portion captured from the first region 20 and a second portion captured from the second region 30. The second region occupies between 5% and 20% of the area of the cropped image (e.g. 10% of the area of the cropped image). This region provides an overlap with the subject's unimpaired visual field to allow the user to correctly place the displayed image with respect to their unimpaired visual field. The extent and location of the area of overlap can be varied depending on the requirements of the subject. For example, for test subject A (shown in FIG. 7), the displayed image can be divided into the first and second region separated by a vertical line. A vertical line is appropriate because test subject A has homonymous hemianopsia classification, with vision lost on the left side of the vertical midline. As shown in FIG. 7, the image capture device is configured such that the majority of its field of view is occupied by the first region 20 and a small part of its field of view overlaps with the second region 30 (in which the subject's visual field is not impaired). Approximately 10% overlap between the displayed field of view (from the camera) and the unimpaired field of view of the subject has been deemed a typically appropriate degree of overlap to allow the subject to correctly place the image, however, this can be optimised for an individual subject.

The precise location and orientation of the display 130 and/or the image capture device 120 can be customised for individual subjects based on the specifications of the wearable frame 110 and the requirements of the user.

In at least some embodiments, as shown in FIG. 5B, the image capture device 120 can be advantageously mounted on a nose bridge portion 115 of the bridging portion 114 of the wearable frame 110. In such embodiments, the image capture device 120 can be configured to have a wide field of view, encompassing all or most of the normal unimpaired human visual field 10 (as shown in FIG. 1). The image displayed by the display unit 130 can then cropped to tailor it to the user's needs without the need to reposition of the image capture device 120. Alternatively, the image capture device can be oriented to capture the missing field of view, as described above.

In any of the above described embodiments, the display unit 130 can comprise a processor 160 configured to crop the image captured by the image capture device 120, according to subject specifications, and display the image cropped image on the display 132. Such an arrangement may be advantageous because such devices can be individually tailored to a subject's needs (based on patient information identifying the extent of visual field loss) without the need to modify the construction of the device 100. A storage medium can also be incorporated into the device 100. The storage medium can allow for patient information (regarding the extent of visual field loss) to be uploaded, on which the cropping information can be based.

To further tailor the device 100 according to the present invention to the user's needs, the frame 110 and/or other components of the device can be manufactured using an additive manufacturing technique (e.g. 3D printing). The configuration and placement of a rechargeable power source 150 (see FIGS. 5A and 5B) can also be tailored according to the user's requirements. For example, the power source 150 can be configured for inductive charging, thereby providing improved wearability characteristics, such as freedom from wires and a waterproof or water-resistant device.

FIG. 7 shows a schematic of test subject A wearing the device 100 described above. As shown in FIG. 7 (and discussed further with reference to FIG. 4), without the device, subject A's visual field is limited to the second region 30 in which vision is deemed to be unimpaired. In the first region 20, the visual field is identified as impaired. As shown in FIG. 7, for test subject A, device 100 is configured such that image capture device 120 captures the first region 20, i.e. at least part of the first region 20 falls within the field of view 40 of the image capture device 120. The display unit 130 is configured to project the captured image from the image capture device 120 onto the uncompromised region of the retina of the subject (e.g. the region corresponding to region 30a as shown in FIG. 3A or the region corresponding to region 30b as shown in FIG. 3B). By delivering an image captured from the lost visual field via an uncompromised visual pathway, the user is able to observe images from the impaired or missing part of the visual field. Of course, because the captured image is delivered to only one of the subject's eyes, the subject is still able to see the second region 30 of the visual field, undisturbed, with the other eye.

Figure 8:
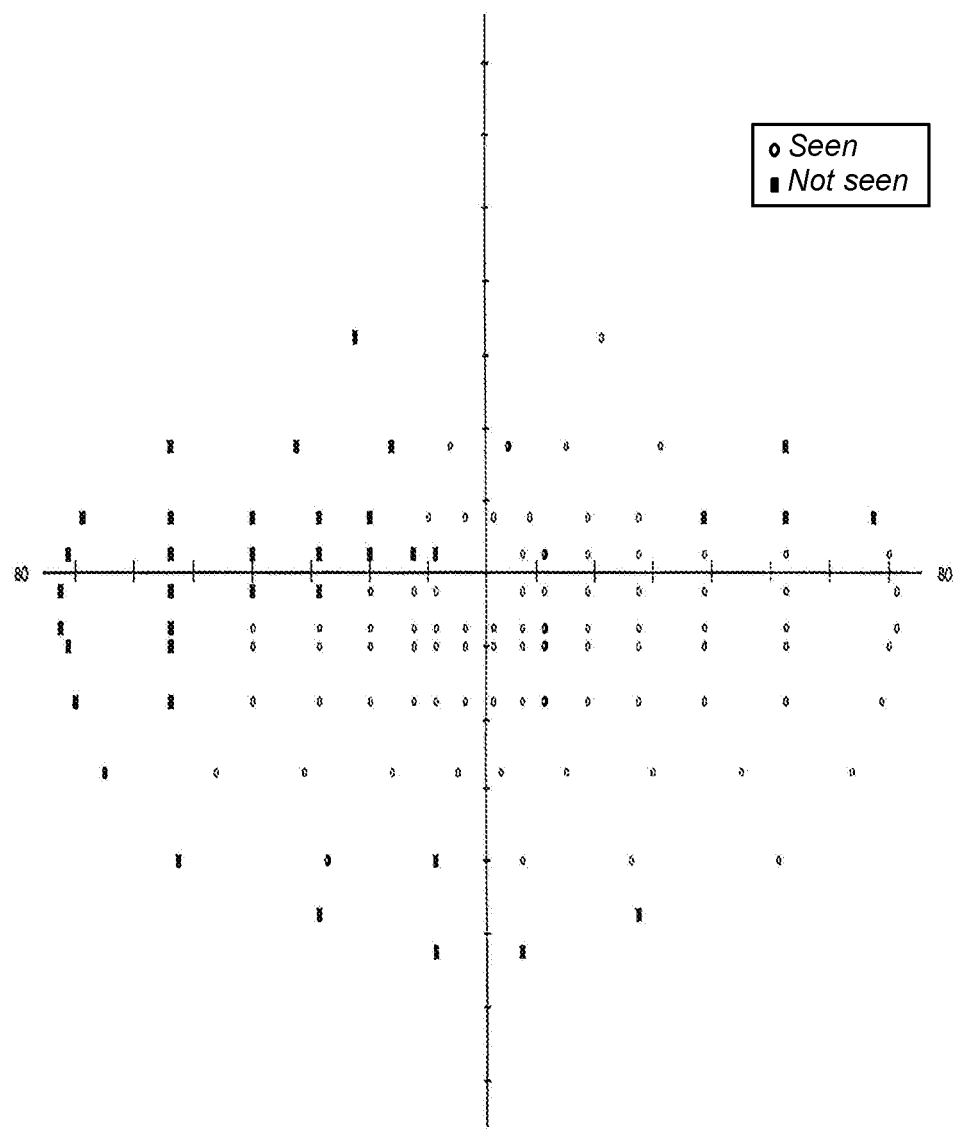
FIG. 8 shows the results of a binocular visual field test for the test subject A wearing a device according to the present invention.

Referring now to FIG. 8, a second static perimetry test under the same conditions as described above was carried out for subject A whilst wearing the device 100. As shown in FIG. 8, the extent of the visual field subject A was able to perceive was improved. In the second test, of the 60 light spots shown to the left of the vertical centreline of the screen, subject A was able to perceive 29 (compared to 10 perceived without the device 100). The four light spots that the user could not perceive in the upper right quadrant were due to placement of the display unit 130 obscuring a small portion of the user's unimpaired visual field 30. Further development of the device 100 can be made to address this issue by optimising the configuration of the display unit 130 to minimise impact upon the user's unimpaired visual field by the display 132.

The device worn by test subject A during the second static perimetry test carried out for subject A was customised for subject A on the basis of her hemianopsia classification: homonymous hemianopsia (left side). Therefore, the image capture device was positioned to capture the left part of the visual field and the display unit was configured to deliver the captured image to the nasal retina of the right eye (a portion of the retina to the right of the centreline in the right eye) (see FIG. 7). However, further improvements to the perceived visual field of affected subjects can be made by tailoring the position of the image capture device 120 (and/or the display device) based on individual visual field maps, such as those shown in FIGS. 2 and 3A and 3B.

A method for manufacturing and customising devices according to the present invention will now be described with reference to FIG. 9. As shown schematically in FIG. 9, a method of manufacturing a device for compensating for loss of part of the visual field of a subject can comprises the steps of: providing patient information identifying (i) a first region 20 of the subject's visual field in which the vision is identified as impaired and (ii) a second region 30 of the subject's visual field in which vision is identified as non-impaired; providing a wearable frame 110 comprising a first arm 112a, a second arm 112b and a bridging portion 114 configured to extend between the first arm 112a and the second arm 112b and rest on the face of the subject; based on the identification of the first region 20, mounting an image capture device 120 on the wearable frame 110 to capture an image from the first region 20 of the subject's visual field; based on upon identification of the second region 30, mounting an image display unit 130 on the frame to project the captured image onto a region of the subject's retina that corresponds to the second region 30 of the subject's visual field. (i) providing a wearable frame comprising a first arm, a second arm and a bridging portion configured to extend between the first arm and the second arm and rest on the face of the subject; (ii) configuring an image capture device on the frame to capture an image from a first region of the subject's visual field; (iii) positioning an image display unit comprising a display on the frame, the display being configured to display an image captured by the image capture device; (iv) providing an optical element configured to project the image from the display onto a region of the subject's retina that is uncompromised, i.e. a region of the retina that corresponds to a second region of the subject's visual field which is identified as unimpaired. The image displayed by the display unit is preferably a live video feed from the image capture device. The region of the retina onto which the image is displayed is an uncompromised region of the retina. This can be determined using monocular static perimetry or other suitable tests that will be apparent to the person skilled in the art in light of the present disclosure.

The patient information provided in the first step of the method can comprise classification information or the results of an individualised visual field test. For example, the patient information may comprise a hemianopsia classification (such as homonymous/left-side, homonymous/right-side, quadrantic/upper-left quadrant, quadrantic/upper-right quadrant, etc.). Although not strictly due to hemianopsia, a hemianopsia clarification can also be determined for subjects with near or total blindness in one eye (e.g. visual field loss is experienced in the region between 60 degrees and 95 degrees temporally from the midline—as shown in FIG. 1). Alternatively or additionally, the patient information can comprise an individualised visual field map (e.g. as shown in FIG. 2 and/or FIGS. 3A and 3B). By customising the device according to patient information indicating the extent and/or region of visual field loss, devices according to the present invention can be used to deliver an image from the lost region of visual field to a region of the user's retina that is uncompromised, thereby restoring perception of the missing visual field to the user. Because the captured image is projected into one eye, the captured image does obscure the subject's surviving unimpaired visual field. The extent of perceivable visual field is thus improved for the subject.

The first and second regions of the subject's visual field can be identified through perimetry testing or another suitable method, as described above. Although methods according to the present invention can additionally comprise the steps of acquiring patient information via perimetry testing (or another suitable method), the skilled person will appreciate that patient data indicating the degree and location of visual field loss can be provided from an external source. In some embodiments, devices according to the present invention can be configured based on patient data that comprises a hemianopsia classification (e.g. homonymous hemianopsia, super/inferior hemianopsia, quadrantic hemianopsia, etc.). In further embodiments, devices according to the present invention can be configured based on patient data that comprises an individualised visual field map (e.g. monocular or binocular data as described with reference to FIGS. 2, 3 and 4). In either case, the image capture device should be configured such that it captures the subject's missing field of view (when the subject is wearing the device) and the display unit should be configured to project the image onto an uncompromised region of the subject's retina. In any event, the patient information comprises information identifying at least one of: (i) a first area of visual field in which vision is identified as impaired; and (ii) a second area of visual field in which vision is identified as unimpaired (if only (i) or (ii) is provided to the device, the other area can be determined by extension).

By identifying the area of the visual field in which vision is impaired, it is possible to identify a first region of the subject's retina corresponding to the region in which vision is identified as impaired and a second region of the subject's retina corresponding to the region in which vision is identified as non-impaired. This information allow the device 100 to be configured to project the captured image onto a region on the retina that is uncompromised and that will allow the subject to perceive the displayed image. It will be appreciated that in embodiments of the invention, uncompromised regions of the retina can be determined by extrapolation from binocular perimetry testing or directly through monocular perimetry testing.

It will be appreciated that the step of configuring the image capture device to capture the first region 20 can be achieved in different ways. For example, the image capture device can be oriented such that it is directed towards the missing field of view. In the case of test subject A, the image capture device was directed towards the left half of the subject's visual field. In other embodiments, the image capture device can be configured to capture substantially all of the unimpaired visual field (region 10 in FIG. 1). The image can then be cropped to correspond more closely to the missing portion of the visual field (region 20 in FIG. 4). In either case, the image capture device captures the missing visual field and the display unit displays the missing view to the subject in a manner that they are able to perceive, i.e. the display unit projects the captured image onto an uncompromised region of the retina.

In some embodiments, the method can further comprise the step of configuring the display unit and/or the processor to crop the captured image based on the patient information. Alternatively, the image capture device can simply be oriented in such a way that it captures the required (missing) visual field. Orienting the camera or cropping the image based on the patient information allow the missing field of view to be prioritised on the display, reducing redundancy. For this reason, the step of cropping can include cropping the image to correspond to the region identified as impaired (e.g. region 20 in FIG. 4). Although it is advantageous to prioritise the missing field of view for display by the display unit, the display need not be limited to the missing field of view. Advantageously, the cropping step includes cropping the captured image such that the captured image extends beyond the area identified as being vision impaired. This provides a region of overlap with an area of the visual field identified as non-impaired, which allows the user to correctly place the displayed image relative to rest of their visual field. Preferably, the displayed image overlaps with the missing along at least one edge. For example, the degree of overlap may be between 5-20%, e.g. 10% in the form of a strip extending along the vertical edge of the image.

The customisation process can include positioning of the image capture device based on patient information. In particular, the image capture device can be advantageously positioned such that (when the device is worn by a subject) the image capture device (i) captures missing field (first region 20); and (ii) does not obscure the user's view of the unimpaired field (second region 30). To this end, the image capture device can be placed in the bridging portion of the frame (e.g. see FIG. 5B).

Additionally or alternatively, the customisation process can advantageously include positioning and configuring the display unit such that (i) the display unit obscures as little as the user's unimpaired field (second region 30) as possible; and/or (ii) the displayed image is projected onto an uncompromised region of the retina. These objectives can be met by appropriate configuration of the display and/or the optical element.

In some embodiments, the device can be provided with processing means and software configured to crop the image according to input patient information. For example, software can be incorporated that automatically displays an appropriate region of the visual field based on input patient data. A storage medium can be provided, which is configured to store patient information and can be updated as necessary.

In some embodiments, the method can further include an optimisation step based on patient data gathered whilst the user is wearing a device 100 according to the present invention. For example, following initial customisation of the device, described above, a perimetry test can be carried out by the subject, this time using the device 100. The results of the perimetry test can then be used to optimise the configurations of the display, the placement, orientation and cropping of the image capture device, the configuration of the optical element, etc. to further optimise the device for the individual user. Such steps can be repeated iteratively until the device 100 is customised according to the user's specifications.

In at least some embodiments, the frame 110 can be further customised according to the subject's needs. For example, prescription lenses 116 may be incorporated into the wearable frame 110 to address long- or short-sightedness in the user (or another sight deficiency that can be corrected with lenses). The wearable frame 110 can also be customised according to subject-specifications, for example, by 3D printing. Customisation of the frame may be necessary in order to appropriately configure the image capture device 120 and the display unit 130 depending on the user's visual field loss.

FIG. 10 shows schematically the steps of a method for compensating for partial loss of visual field in a subject. As shown in FIG. 10, methods according to the present invention comprise the steps of: (a) providing patient information identifying (i) a first area (20) of the subject's visual field in which the subject's visual field is identified as impaired and (ii) a second region (30) of the visual field in which the subject's visual field is identified as non-impaired; (b) capturing an image from the first area of the subject's visual field using an image capture device (120); (c) cropping the captured image based on image cropping information, wherein the image cropping information is based on the first region (20) as identified in step (a); (d) projecting the cropped image onto a region of the subject's retina that corresponds to the second region (30) of the subject's visual field as identified in step (a). The step of identifying the impaired and unimpaired regions of the subject's vision can be carried out as described above. The cropping step (step (ii)) can also be carried out in the manner described above.

The present invention has been described above with respect to a number of illustrative embodiments, which the skilled person will understand represent one way in which the invention may be put into effect. For example, although the present invention has been demonstrated with reference to test subject A, who suffers from homonymous hemianopsia (left side), the skilled person will appreciate that the present invention is applicable to other types of visual field loss. In particular, because the present invention provides devices and methods that can be tailored individually to a subject, the present invention can be used to compensate for many types of partial visual field loss.

In addition to being applicable to many types of visual field loss, the embodiments described above illustrate examples of how the invention may be put into effect. Other means of putting the invention into effect will be apparent to the skilled person. As such, the illustrative embodiments described above may be modified without departing from the scope of the present invention.

The following embodiments also form part of the present invention:

Embodiment 1

A device for compensating for partial loss of visual field in a subject, the device comprising:

a wearable frame comprising a first arm, a second arm and a bridging portion configured to extend between the first arm and the second arm and rest on the face of the subject;

an image capture device supported by the wearable frame and configured to capture an image from a first region of the subject's visual field;

a display unit configured to project the captured image onto a region of a retina of the subject corresponding to a second region of the subject's visual field;

wherein the first region of the subject's visual field is identified as a region of the subject's visual field in which the subject's vision is impaired and the second region of the visual field is identified as a region of the subject's visual field in which the subject's vision is deemed non-impaired.

Embodiment 2

The device according to Embodiment 1, wherein the display unit is configured to crop the image based on stored cropping information before projecting the image onto the region of the retina of the subject, wherein the stored cropping information is based on patient information identifying the first region and the second region of the visual field.

Embodiment 3

The device according Embodiment 2, wherein the cropped image extends beyond the first region to provide at least one region of overlap with the second region.

Embodiment 4

The device according to Embodiment 3, wherein the cropped image comprises a first portion captured from the first region and a second portion captured from the second region, and wherein the second region occupies between 5% and 20% of the area of the cropped image (e.g. 10% of the area of the cropped image).

Embodiment 5

The device according to Embodiment 1, wherein the display unit comprises a display configured to display the captured image and an optical element configured to project the image onto the region of the subject's retina.

Embodiment 6

The device according to Embodiment 1, wherein the display unit comprises a screen and/or a projector.

Embodiment 7

The device according to Embodiment 1, wherein the display unit comprises a lens, a prism, a mirror or any combination thereof.

Embodiment 8

The device according to Embodiment 1, wherein the device further comprises a rechargeable power source.

Embodiment 9

A method for manufacturing a device for compensating for partial loss of visual field in a subject, the method comprising:

providing patient information identifying (i) a first region of the subject's visual field in which the vision is identified as impaired and (ii) a second region of the subject's visual field in which vision is identified as non-impaired;

providing a wearable frame comprising a first arm, a second arm and a bridging portion configured to extend between the first arm and the second arm and rest on the face of the subject;

based on the identification of the first region, mounting an image capture device on the wearable frame to capture an image from the first region of the subject's visual field;

based on upon identification of the second region, mounting an image display unit on the frame to project the captured image onto a region of the subject's retina that corresponds to the second region of the subject's visual field.

Embodiment 10

The method according to Embodiment 9, wherein the patient information comprises a hemianopsia classification.

Embodiment 11

The method according to Embodiment 9, wherein the patient information comprises an individualised visual field map identifying at least one of: (i) the first area of the subject's visual field in which vision is identified as impaired; and (ii) the second area of the subject's visual field in which vision is identified as non-impaired.

Embodiment 12

The method according to Embodiment 9, further comprising the step of mapping the subject's visual field and identifying (i) the first area of visual field in which vision is identified as impaired; and (ii) the second area of visual field in which vision is identified as non-impaired.

Embodiment 13

The method according to Embodiment 9, further comprising the step of configuring the display unit to crop the captured image based on the patient information.

Embodiment 14

The device according to Embodiment 13, wherein the cropped image extends beyond the first region to provide at least one region of overlap with the second region, e.g. an overlap of between 5 and 20%, for example 10%.

Embodiment 15

A method for compensating for partial loss of visual field in a subject, the method comprising:

(a) providing patient information identifying (i) a first area of the subject's visual field in which the subject's visual field is identified as impaired and (ii) a second region of the visual field in which the subject's visual field is identified as non-impaired;

(b) capturing an image from the first area of the subject's visual field using an image capture device;

(c) projecting the captured image onto a region of the subject's retina that corresponds to the second region of the subject's visual field as identified in step (a).

Embodiment 16

The method according to Embodiment 15, further comprising the step of cropping the captured image before projecting it onto the region of the subject's retina based on the patient information identified in step (a).

Embodiment 17

The method according to Embodiment 15, wherein the patient information comprises at least one of:
a hemianopsia classification; and/or an individualised visual field map identifying at least one of: (i) a first area of visual field in which vision is identified as impaired; and (ii) a second area of visual field in which vision is identified as unimpaired.

Embodiment 18

The method according to Embodiment 16, wherein the display unit is configured to crop the captured image to extend beyond the first region to provide at least one region of overlap with the second region.

Embodiment 19

The method according to Embodiment 16, wherein the method further comprising the step of storing patient information in a storage medium comprised in the device.

Embodiment 20

The method according to Embodiment 15, wherein the display unit is configured to show a live video feed from the image capture device.

The invention claimed is:
1. A device for compensating for partial loss of visual field in a subject, the device comprising:
 a wearable frame comprising a first arm, a second arm and a bridging portion configured to extend between the first arm and the second arm and rest on the face of the subject;
 an image capture device supported by the wearable frame and configured to capture an image from a first region of the subject's visual field;
 a display unit configured to project the captured image onto a region of a retina of the subject corresponding to a second region of the subject's visual field;
 wherein the display unit is configured to crop the image based on stored cropping information before projecting the image onto the region of the retina of the subject, wherein the stored cropping information is based on patient information identifying the first region of the subject's visual field as a region in which the subject's visual field is impaired and the second region of the visual field as a region in which the subject's visual field is non-impaired;
 wherein the display unit is configured to crop the captured image to correspond to the first region; wherein the cropped image extends beyond the first region to provide at least one region of overlap with the second region.
2. The device according to claim 1, wherein the cropped image comprises a first portion captured from the first region and a second portion captured from the second region, and wherein the second region occupies between 5% and 20% of the area of the cropped image.
3. The device according to claim 1, wherein the display unit comprises a display configured to display the captured image and an optical element configured to project the image onto the region of the subject's retina, and the display comprises a screen and/or a projector.
4. The device according to claim 1, wherein the optical element comprises a lens, a prism, a mirror or any combination thereof.
5. The device according to claim 1, wherein the device further comprises a rechargeable power source.
6. The device according to claim 1, wherein the image capture device is mounted on a central portion of the bridging portion of the wearable frame.
7. A method for manufacturing a device for compensating for partial loss of visual field in a subject, the method comprising:
 providing patient information identifying (i) a first region of the subject's visual field in which the vision is identified as impaired and (ii) a second region of the subject's visual field in which vision is identified as non-impaired;
 providing a wearable frame comprising a first arm, a second arm and a bridging portion configured to extend between the first arm and the second arm and rest on the face of the subject;
 based on the identification of the first region, mounting an image capture device on the wearable frame to capture an image from the first region of the subject's visual field;
 based on upon identification of the second region, mounting an image display unit on the frame to project the captured image onto a region of the subject's retina that corresponds to the second region of the subject's visual field,
 configuring the display unit to crop the captured image based on the patient information, wherein the cropped image extends beyond the first region to provide at least one region of overlap with the second region.
8. The method according to claim 7, wherein the patient information comprises at least one of: a hemianopsia classification and an individualised visual field map identifying at least one of: (i) the first area (20) of the subject's visual field in which vision is identified as impaired; and (ii) the second area (30) of the subject's visual field in which vision is identified as non-impaired.
9. The method according to claim 7, further comprising the step of mapping the subject's visual field and identifying (i) the first area of visual field in which vision is identified as impaired; and (ii) the second area of visual field in which vision is identified as non-impaired.
10. A method for compensating for partial loss of visual field in a subject, the method comprising:
 (a) providing patient information identifying (i) a first area of the subject's visual field in which the subject's visual field is identified as impaired and (ii) a second region of the visual field in which the subject's visual field is identified as non-impaired;
 (b) capturing an image from the first area of the subject's visual field using an image capture device;
 (c) cropping the captured image based on image cropping information, wherein the image cropping information is based on the first region as identified in step (a);
 (d) projecting the cropped image onto a region of the subject's retina that corresponds to the second region of the subject's visual field as identified in step (a);
 wherein the display unit is configured to crop the captured image so that the cropped image extends beyond the first region to provide at least one region of overlap with the second region.

11. The method according to claim 10, wherein the step of identifying the first region and the second region of the subject's visual field comprises one or more of: providing patient information comprising a hemianopsia classification and providing patient information comprising an individualised visual field map identifying at least one of: (i) a first area of visual field in which vision is identified as impaired; and (ii) a second area of visual field in which vision is identified as unimpaired.

12. The method according to claim 10, wherein the method further comprising the step of storing patient information in a storage medium comprised in the device.

13. The device according to claim 1, wherein the display unit (130) is configured to show a live video feed from the image capture device (120).

14. The device according to claim 1, wherein at least the frame is formed using an additive manufacturing technique.

15. The method of claim 10, with at least one light source for delivery of photons to an eye for use in the method, wherein the light source of the image display emits photons building up an image onto a region of the subject's retina that corresponds to the second region of the subject's visual field in which the subject's vision is identified as non-impaired, therewith compensating for partial loss of visual field in the subject.

16. The method according to claims 15, wherein the image display comprises at least one light emitting diode comprising the light source and wherein the light source is a semiconductor material such as a p/n semiconductor material.

* * * * *